United States Patent [19]

Quinn, III

[11] 3,974,576

[45] Aug. 17, 1976

[54] HOLDING FRAME FOR FACIAL IDENTIFICATION SYSTEM

[76] Inventor: William T. Quinn, III, 681 Park Ave., Freehold, N.J. 07728

[22] Filed: July 28, 1975

[21] Appl. No.: 599,484

[52] U.S. Cl. .................................. 35/28; 35/62; 40/102; 40/156
[51] Int. Cl.² .................. G09B 1/30; G09F 11/06
[58] Field of Search .................. 35/26, 28, 62, 66; 40/102, 156, 158 R; 128/DIG. 15; 229/71; 281/15 R

[56] References Cited
UNITED STATES PATENTS

| | | | |
|---|---|---|---|
| 1,998,640 | 4/1935 | Shaw | 40/158 R |
| 2,791,040 | 5/1957 | Santorelli | 35/62 |
| 2,891,326 | 6/1959 | Fransson | 35/62 |
| 3,353,281 | 11/1967 | Schulze | 35/28 |
| 3,659,843 | 5/1972 | Kojigian | 128/DIG. 15 UX |
| 3,837,106 | 9/1974 | Lofstrom | 40/156 X |

FOREIGN PATENTS OR APPLICATIONS 1,137,088  12/1968  United Kingdom ............... 35/28

*Primary Examiner*—Harland S. Skogquist
*Attorney, Agent, or Firm*—Sughrue, Rothwell, Mion, Zinn & Macpeak

[57] ABSTRACT

A frame for holding the components of a facial identification system, wherein the system utilizes changeable components enabling a witness to direct construction of a representation of a face, has a back plate and a transparent cover plate. The back plate has positioning strips thereon contacted by at least some of the components. The back plate and cover plate are connected releasably at their side edges by combined hinge and closure straps which are adjustable as to tension. The straps are engaged on affixation pads secured to the plates.

5 Claims, 3 Drawing Figures

HOLDING FRAME FOR FACIAL IDENTIFICATION SYSTEM

CROSS-REFERENCE TO RELATED APPLICATION

This invention relates to an improvement on the subject matter of my prior application Ser. No. 423,697, now U.S. Pat. No. 3,896,565.

BACKGROUND OF THE INVENTION

1. Field of the Invention

This invention relates to a holding frame for changeable components, hinged at either side thereof, alternatively, and of variable compression as to materials placed therebetween.

2. Statement of the Prior Art

Reference is made to my aforesaid prior patent for a description of prior art as to systems of this general type. Hinged holders for such systems are also known wherein a piano hinge holds a cover at one side, and a removable clip is provided for the other side, the base of the holder being, in such prior art, provided with a series of notches or slots for the components.

SUMMARY OF THE INVENTION

The present invention provides a means for assembly of the components of a facial identification system, to display the completed representation. The frame provides guide strips for uniformly and neatly positioning the components, and provides also a unique, alternatively acting hinge and closure means.

The feature of variable compression occasioned hereby obscures lines of connection between the components. Moreover, the tight compression and the means for achieving such compression eliminate the possibility of disarrangement of a completed composite.

The fabrication of the frame body portion and cover plate from clear plastic make it possible to mark on the frame when required, with an erasable crayon or the like, and to subsequently clean the frame for re-use.

In some circumstances, the frame sections may be tinted in order to change the texture of the picture formed by the components.

The device hereof further obviates fixed hinges and clips which tend to wear out and to become lost.

Other and further objects and advantages of the invention will become apparent to those skilled in the art from a consideration of the following specification when read in conjunction with the annexed drawing.

DESCRIPTION OF THE PREFERRED EMBODIMENT

Figure 1:
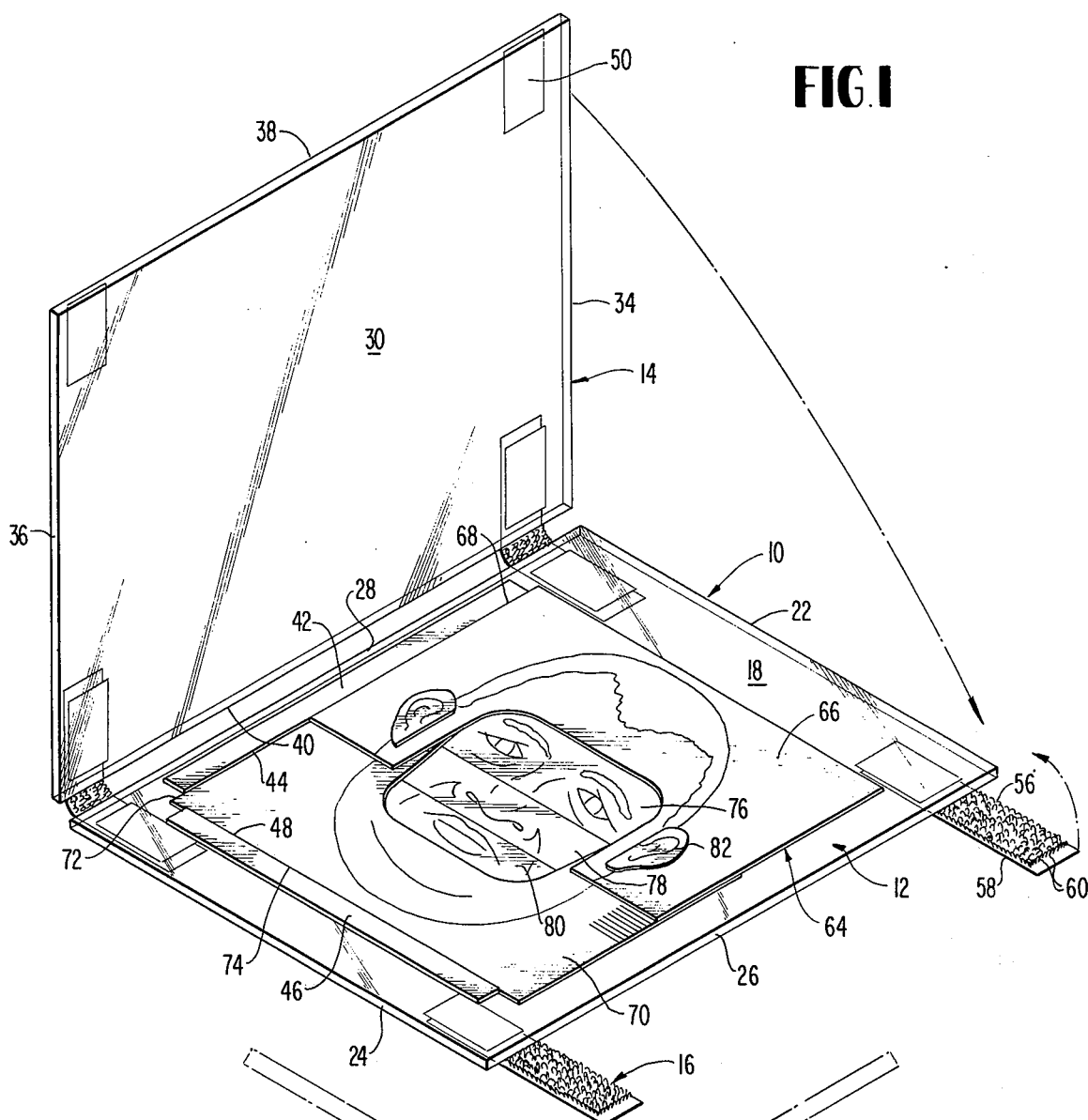
FIG. 1 is a perspective view showing a frame and facial identification system in accordance with this invention.
Figure 3:
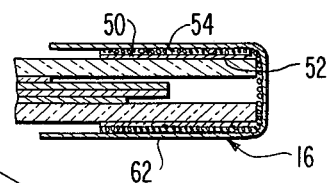
FIG. 3 is an enlarged detail view in cross-section of the hinge and closure straps in use.

Referring to the drawing in more detail, a frame in accordance herewith is shown and generally identified by reference numeral 10. The frame 10 comprises a body portion 12, a cover plate 14, and a series of hinge/closure means 16.

The back plate 12 comprises a substantially rectangular sheet of clear plastic material or the like, having an inner surface 18, an outer surface 20, top and bottom edges 22, 24, and first and second side edges 26, 28. The cover plate 14 is of identical dimension and material fabrication, and has an inside surface 30, an outside surface 32, upper and lower edges 34, 36, and cover plate first and second side edges 38, 40. The back plate and cover plate are hingedly secured to one another, as described below, with the first side edge 26 of the back plate and first side edge 38 of the cover plate in corresponding positions, and the respective second side edges 28 and 40 similarly located. The top and upper edges 22, 34, and bottom and lower edges 24, 36, are also in alignment.

The back plate has a vertical strip 42 of positioning material secured to its inner surface 18. The strip 42 is substantially rectangular, and includes a positioning face 44. The strip is situated adjacent and substantially parallel to the second side edge of the back plate. Also located on the inner surface 18 of the back plate 12 is a horizontal strip 46 of positioning material. The horizontal strip is located in spaced, substantially perpendicular relation to the vertical strip, and is substantially parallel to the bottom edge 24 of the back plate. The horizontal strip has a positioning face 48.

The hinge and closure means 16 provided hereby includes a plurality of affixation pads 50. The pads 50 each have a backing 52 which is adhesively bonded to the respective outer surfaces 20 and 32 of the back plate and cover plate at corner locations adjacent the side edges. The pads have exposed felt-like outer faces 54 of a fibrous, hirsute substance. The pads of the back plate and cover plate are arranged in superposed pairs when the cover plate is placed on the back plate. Coacting with the pads is a plurality of hinge and closure straps 56. These straps each have an inner face 58 from which extend a series of closely spaced, hook-like projections 60. The straps also have a flexible outer cover 62. The material of fabrication of the straps is that sold under the trademark VELCRO, and is commercially available. Such material has the characteristic of temporary adhesion to fibrous material such as the material forming the faces 54 of the pads.

The facial representation 64 is made up from a number of components as described in my aforesaid prior patent, which may or may not include other means for temporary adhesion to one another. For purposes of description and orientation herein, these include a top head component 66 having an inside edge 68, a bottom jaw component 70 with an inside edge 72 and bottom edge 74, and intermediate eye, nose, and mouth components 76, 78, and 80. Separable ear components 82 are also provided. The eye, nose, and mouth components have inner edges which are not shown in the drawing. The bottom jaw component is positioned with its bottom edge 74 in contact with the face 48 of the horizontal positioning strip 46, and its inside edge 72 against the face 44 of the vertical strip 42. The eye, nose, and mouth components, and the top head component also have their respective inner edges in contact with the face 44 of the strip. This uniformly and correctly orients these components, and permits instant reconstruction if the facial representation falls into disarray for any reason.

Figure 2:
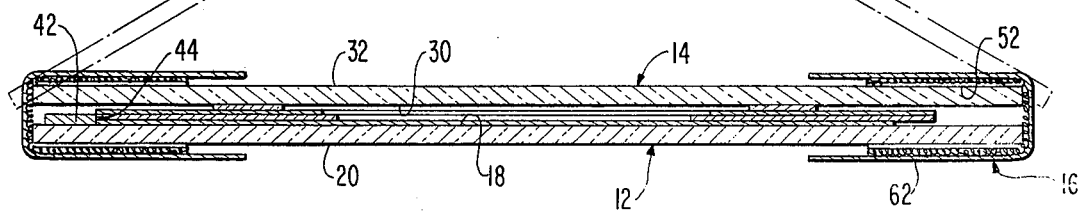
FIG. 2 is a lateral cross-sectional view, showing the unit in closed position in full lines, and showing alternate open positions in phantom lines.

With the representation 64 constructed and positioned as aforesaid, the cover plate 14 is placed in superposed position on the back plate. The straps 56 are then secured to the pads on either the back plate or cover plate and stretched tightly for engagement on the other pads of the pairs. As shown in FIG. 2, the cover plate may be readily pivoted from either side, and the tension is of course, adjustable to any degree within the range permitted by the length of the straps and the thickness of material between the plates.

I claim:

1. A holding frame for strips of flat material comprising an array of components making up a representation, the frame comprising:
   a back plate, and a cover plate superposed over the back plate;
   the back plate and cover plate including outer surfaces;
   a series of affixation pads secured to the outer surfaces of the back plate and cover plate;
   the affixation pads being arranged in superposed pairs;
   a plurality of straps having means thereon for temporary adhesion to the pads; and
   the straps being engaged on the pairs of pads to provide alternative hinge and closure means for the back plate and cover plate.

2. The invention of claim 1, and:
   a series of positioning strips for the components on said back plate.

3. A facial identification system holding frame for handling and display of a composite facial representation made up of a group of individual components, the holding frame comprising:
   a back plate having an inner surface, an outer surface, top and bottom edges and first and second side edges;
   a cover plate having an inside surface, an outside surface, upper and lower edges, and cover plate first and second side edges;
   a vertical strip of positioning material secured to the inner surface of the back plate adjacent and substantially parallel to the second side edge thereof;
   a horizontal strip of positioning material secured to the inner surface of the back plate and spaced, in substantially perpendicular relation to the vertical strip and in substantially parallel relation to the bottom edge thereof;
   a plurality of affixation pads, each having an outer face of a fibrous, hirsute substance, the pads being fixedly secured on the outer surface of the back plate and on the outside surface of the cover plate in superposed pairs adjacent the respective side edges of the back plate and cover plate;
   a plurality of hinge and closure straps each having an inner face from which extend a series of closely spaced hook-like projections;
   said components being positioned on said back plate as said composite facial representation, with at least some of said components in contact with one or more of the strips of positioning material; and;
   one of the hinge and closure straps being engaged with each of said pairs of affixation pads.

4. The invention of claim 3, wherein:
   the hinge and closure straps are arranged such that, when the strips at said adjacent side edges of the back plate and cover plate are disengaged from the pads, the remaining straps serve as hinges for the opposite side edges.

5. The invention of claim 3, wherein:
   the straps are of a length to permit adjustable pressure between the back plate and cover plate.

* * * * *